United States Patent
Pop et al.

(10) Patent No.: US 8,290,111 B1
(45) Date of Patent: Oct. 16, 2012

(54) ELECTROCHEMICAL CORROSION POTENTIAL DEVICE AND METHOD

(75) Inventors: Mihai G. M. Pop, Lynchburg, VA (US); Brian G. Lockamon, Evington, VA (US); Hans-Jürgen Sell, Hemhofen (DE); Renate Kilian, Fürth (DE)

(73) Assignees: Areva NP Inc., Lynchburg, VA (US); Areva NP GmbH, Erlangen (DE)

( * ) Notice: Subject to any disclaimer, the term of this patent is extended or adjusted under 35 U.S.C. 154(b) by 811 days.

(21) Appl. No.: 11/807,316

(22) Filed: May 25, 2007

Related U.S. Application Data

(63) Continuation-in-part of application No. 10/951,531, filed on Sep. 28, 2004, now abandoned.

(51) Int. Cl.
*G21C 17/00* (2006.01)

(52) U.S. Cl. .................. 376/259; 376/245; 376/247

(58) Field of Classification Search .................. 376/245, 376/305, 306; 422/53; 205/775.5, 776, 776.5; 324/700
See application file for complete search history.

(56) References Cited

U.S. PATENT DOCUMENTS

| | | | |
|---|---|---|---|
| 3,284,310 A | 11/1966 | Straat | |
| 3,988,565 A | 10/1976 | Hill | |
| 4,155,814 A * | 5/1979 | Tejfalussy et al. | 205/776 |
| 5,130,080 A | 7/1992 | Niedrach | |
| 5,171,517 A * | 12/1992 | Solomon et al. | 376/245 |
| 5,353,650 A | 10/1994 | Barshay et al. | |
| 5,425,871 A * | 6/1995 | Jayaweera et al. | 204/435 |
| 5,848,113 A | 12/1998 | Kim et al. | |
| 5,854,818 A * | 12/1998 | Van Swam et al. | 376/409 |
| 5,896,432 A | 4/1999 | Kim et al. | |
| 6,181,760 B1 | 1/2001 | JinKim | |
| 6,222,307 B1 | 4/2001 | Roy et al. | |
| 6,278,756 B1 | 8/2001 | JinKim | |
| 6,320,395 B1 | 11/2001 | Bosch et al. | |
| 6,391,173 B1 | 5/2002 | Kim et al. | |
| 6,411,667 B2 | 6/2002 | Kim et al. | |
| 6,610,185 B2 | 8/2003 | Kim et al. | |
| 6,623,611 B1 | 9/2003 | Jett et al. | |
| 6,683,463 B2 | 1/2004 | Yang et al. | |
| 6,744,265 B2 | 6/2004 | Yunovich et al. | |
| 2004/0009455 A1 * | 1/2004 | Chiang et al. | 434/218 |

FOREIGN PATENT DOCUMENTS

EP          0 499 217          8/1992

(Continued)

OTHER PUBLICATIONS

Kim et al., "Data Quality, Issues, and Guidelines for Electrochemical Corrosion Potential Measurement in High-Temperature Water", Corrosion Science Section, NACE International, presented as paper No. 01137 at CORROSION/2001, Mar. 2001, Houston, TX (USA).*

(Continued)

*Primary Examiner* — Ricardo Palabrica
*Assistant Examiner* — Marshall O'Connor
(74) *Attorney, Agent, or Firm* — Kenyon & Kenyon LLP

(57) ABSTRACT

The invention provides at least two electrochemical sensors positioned in a nuclear reactor or in a system adjacent to the nuclear reactor, wherein at least one of the at least two electrochemical sensors has a heated zirconium electrode, and the at least two electrochemical sensors produce voltages proportional to an electrochemical corrosion potential for a surface that each of the at least two electrochemical sensors are installed upon. The invention also provides an arrangement configured to accept the voltages produced by the at least two electrochemical sensors, wherein the arrangement is configured to determine an electrochemical corrosion potential of a zirconium fuel rod in the nuclear reactor based upon the voltages of the at least two electrochemical sensors.

9 Claims, 5 Drawing Sheets

FOREIGN PATENT DOCUMENTS

| EP | 0 417 571 | 5/1995 |
|---|---|---|
| JP | 2000 065785 | 3/2000 |
| WO | WO 2006/135391 | 12/2006 |

OTHER PUBLICATIONS

Hettiarachchi, S., "Advances in Electrochemical Corrosion Potential Monitoring in Boiling Water reactors", Proceedings of the 12th International Conference on Environmental Materials in Nuclear Power System—Water Reactors, Salt Lake City, UT, Aug. 14-18, 2005.*

Dr. Michael P. Manahan, Sr., Electrochemical Corrosion Potential (ECP) Probes (www.mpmtechnologies.com).

PCT International Search Report and Written Opinion from PCT/US2007/014599, mailed on Jun. 11, 2008.

PCT International Search Report and Written Opinion from PCT/US2005/028842, mailed on Aug. 29, 2008.

Supplementary European Search Report from European Patent Application No. 05857909.5 mailed on Oct. 13, 2010.

* cited by examiner

ELECTROCHEMICAL CORROSION POTENTIAL DEVICE AND METHOD

CROSS-REFERENCE TO RELATED APPLICATION

This application is a continuation-in-part application of U.S. patent application Ser. No. 10/951,531 filed Sep. 28, 2004 now abandoned, which is incorporated herein by reference.

FIELD OF THE INVENTION

The current invention relates to the determination of electrochemical corrosion potential for components in a nuclear power plant. More specifically, the current invention provides a device and method for determination of electrochemical corrosion potential for both zirconium fuel rods and various structural materials (of the nuclear plant system) at the reactor water temperature in a reactor coolant system for a nuclear power plant, wherein the electrochemical corrosion potential is determined through potential measurements remote from the fuel rod.

BACKGROUND INFORMATION

Nuclear reactors, for example boiling water and pressurized water reactors, pass water through a reactor core which contains nuclear fuel. The passing of this water through the reactor core heats the water. The water is heated to either a hot liquid phase (pressurized water) or a combination of a hot liquid phase and a vapor phase (boiling water). The water and/or steam are transported through systems in the nuclear power plant, such as the reactor pressure vessel, steam separators, pressurizers and steam generators to transfer the heat energy generated by the nuclear reaction to other working systems. These piping systems and components transporting the fluid are made of various materials which may be susceptible to corrosion and irradiation induced or assisted stress corrosion cracking.

Electrochemical corrosion potential ("ECP") provides a guide to determining an amount of a oxidation/reduction reaction which occurs on a metal surface, for example on the surface of primary water coolant pipes. The oxidation/reduction reactions may depend, for example, on a dissolved oxygen concentration of water in a nuclear reactor, hydrogen concentration and/or hydrogen peroxide concentration obtained during water radiolysis. To decrease the electrochemical corrosion potential of these reactor coolant systems, the dissolved oxygen, and hydrogen peroxide concentrations of the water are kept as low as possible, preferably, to a level of about 25 parts per billion. This is performed, for example, by adding hydrogen to the system. Practically, however, maintaining dissolved oxygen, hydrogen and hydrogen peroxide concentrations at this low level is extremely difficult due to the changing water chemistry in the reactor coolant system.

Electrochemical corrosion potential measurements are made in nuclear power stations to determine whether corrosive conditions are occurring in the station and whether stress corrosion cracking is likely to occur. In particular, if the electrochemical corrosion potential value is relatively low (i.e. below a threshold value), corrosion rate and/or stress corrosion crack growth rates are not significant. Above the threshold value, however, the possibility of stress corrosion cracking and/or the corrosion rate increases when electrochemical corrosion potential values increase. Measurements of electrochemical corrosion potential are made at a single point in the primary coolant system on the materials of interest such as in the weakest materials of internals. Existing electrochemical potential probes contain sensors that are typically a metal to metal oxide configuration which respond to oxygen concentrations in the reactor water.

Existing systems used to measure electrochemical corrosion potential have many drawbacks. First, the probes used are fragile and are only operable for approximately three months as the sensors within the probes deteriorate from heat and radiation. As a consequence, the probes can only measure the electrochemical corrosion potential for less than 25% of the resident reactor core time precluding their usage around a nuclear reactor. Nuclear power plant operators' alternatives to alleviate this drawback are few. The nuclear power plant may be operated without monitoring corrosive conditions, however if the electrochemical corrosion potential is not measured for the entire fuel cycle, conditions may favor the formation of corrosion or stress corrosion cracking, thereby potentially damaging sensitive and expensive nuclear power plant systems. Alternatively, the nuclear reactor may be shut down and the electrochemical corrosion potential probes around the reactor are replaced. This alternative is economically unattractive due to the economics of a facility closure. The second drawback is that existing systems use a discrete measurement point probe for analysis. This type of system merely provides a spot measurement on an individual system. Existing systems cannot ascertain if the electrochemical corrosion potential is elevated in a part of the nuclear plant system not directly measured. The complex and changing materials through a nuclear power plant coolant system do not allow current systems to accurately measure electrochemical corrosion potential of systems relative to one another. As a consequence, certain systems or subsystems of the nuclear reactor are more prone to corrosion and stress corrosion cracking, as compared to others. Current systems do not allow the nuclear plant operator to compare data derived from measuring different systems, therefore attention is focused on the probe location. A true risk assessment analysis of the entire nuclear plant system is not performed. Current systems also do not determine an electrochemical corrosion potential for the zirconium clad fuel elements, as compared with the electrochemical corrosion potential measured for structural internals or piping materials. To date, current systems are limited to determining electrochemical corrosion potential of structural or piping members inside the reactor cooling systems.

There is a need to provide an electrochemical corrosion potential measuring system that will allow for a determination of an electrochemical corrosion potential of the zirconium fuel rods during an entire fuel cycle of a nuclear power plant.

There is a further need to provide an electrochemical corrosion potential measuring system that allows for replacement of a probe and its associated sensors at the end of its service life in a cost efficient manner.

There is also a need to provide an electrochemical corrosion potential measuring system that will determine the electrochemical corrosion potential of various materials (which make up the nuclear plant system) at the same time to provide data to a nuclear plant operator as to which nuclear systems are at risk for corrosion relative to other nuclear systems.

There is also a further need to provide an electrochemical corrosion potential measuring system that may be utilized to determine the amount of potential degradation of fuel rods during reactor operating conditions.

SUMMARY

It is therefore an objective of the present invention to provide an electrochemical corrosion potential measuring system that will allow for determining an electrochemical corrosion potential for both zirconium fuel rods and various structural materials (of the nuclear plant system) at the reactor water temperature during an entire fuel cycle of a nuclear power plant.

It is also an objective of the present invention to provide an electrochemical corrosion potential measuring system that allows for replacement of a probe and its associated sensors at the end of the sensors' respective lifetime in a cost efficient manner.

It is also an objective of the invention to provide an electrochemical corrosion potential measuring system that will allow for determination of electrochemical corrosion potential for several different structural materials of a nuclear power plant to provide data to a nuclear plant operator as to what nuclear systems are at risk for excessive corrosion or for stress corrosion cracking relative to other nuclear systems (based on the materials making up such systems). By measuring the electrochemical corrosion potential of several components throughout the nuclear power plant system, the components closely associated in material type and position would have a similar electrochemical corrosion. Therefore, determining which systems of a nuclear power plant are at risk for corrosion relative to other nuclear systems can be accomplished by comparing the electrochemical corrosion potential of a zirconium fuel rod to that of a zirconium structural element (such as a pipe or other structure), or a stainless steel structural element (such as a pipe or other structure), or some combination thereof. The material structural elements with the highest ECP values will be at the highest risk for corrosion relative to the other material structural elements with the lower ECP values.

It is a still further objective of the present invention to determine the electrochemical corrosion potential of nuclear fuel rods at their operating temperature.

The objectives of the present invention are achieved as illustrated and described. The invention provides a system for determining an electrochemical corrosion potential of a zirconium fuel rod, the system comprising at least two electrochemical sensors positioned either in a nuclear reactor or in a system adjacent to the nuclear reactor, wherein at least one of the at least two electrochemical sensors includes a heated zirconium electrode, and the at least two electrochemical sensors measure voltages proportional to an electrochemical corrosion potential for a surface that each of the at least two electrochemical sensors are installed upon. The system also includes a means for heating the zirconium electrode, and an arrangement configured to accept the voltages produced by the at least two electrochemical sensors, wherein the arrangement is configured to determine an electrochemical corrosion potential of a zirconium fuel rod based upon the voltages of the at least two electrochemical sensors. Preferably, the means for heating the zirconium electrode is a heating sleeve, and the zirconium electrode is heated thereby to a temperature which is approximately equal to that of the fuel rod surface temperature.

The present invention also provides a method for determining an electrochemical corrosion potential of a zirconium fuel rod, the method comprising positioning at least two electrochemical corrosion sensors in either a nuclear reactor or in a system adjacent to the nuclear reactor, wherein at least one of the at least two electrochemical sensors includes a heated zirconium electrode, and producing a voltage between the at least two electrochemical corrosion sensors. The method also includes measuring a current induced by the voltage, and determining an electrochemical corrosion potential of a zirconium fuel rod based upon the current induced. Preferably, the heated zirconium electrode is heated to a temperature which is approximately equal to that of the fuel rod surface temperature. Typically, the fuel rod surface temperature is approximately 400° C.

DETAILED DESCRIPTION

Figure 1:
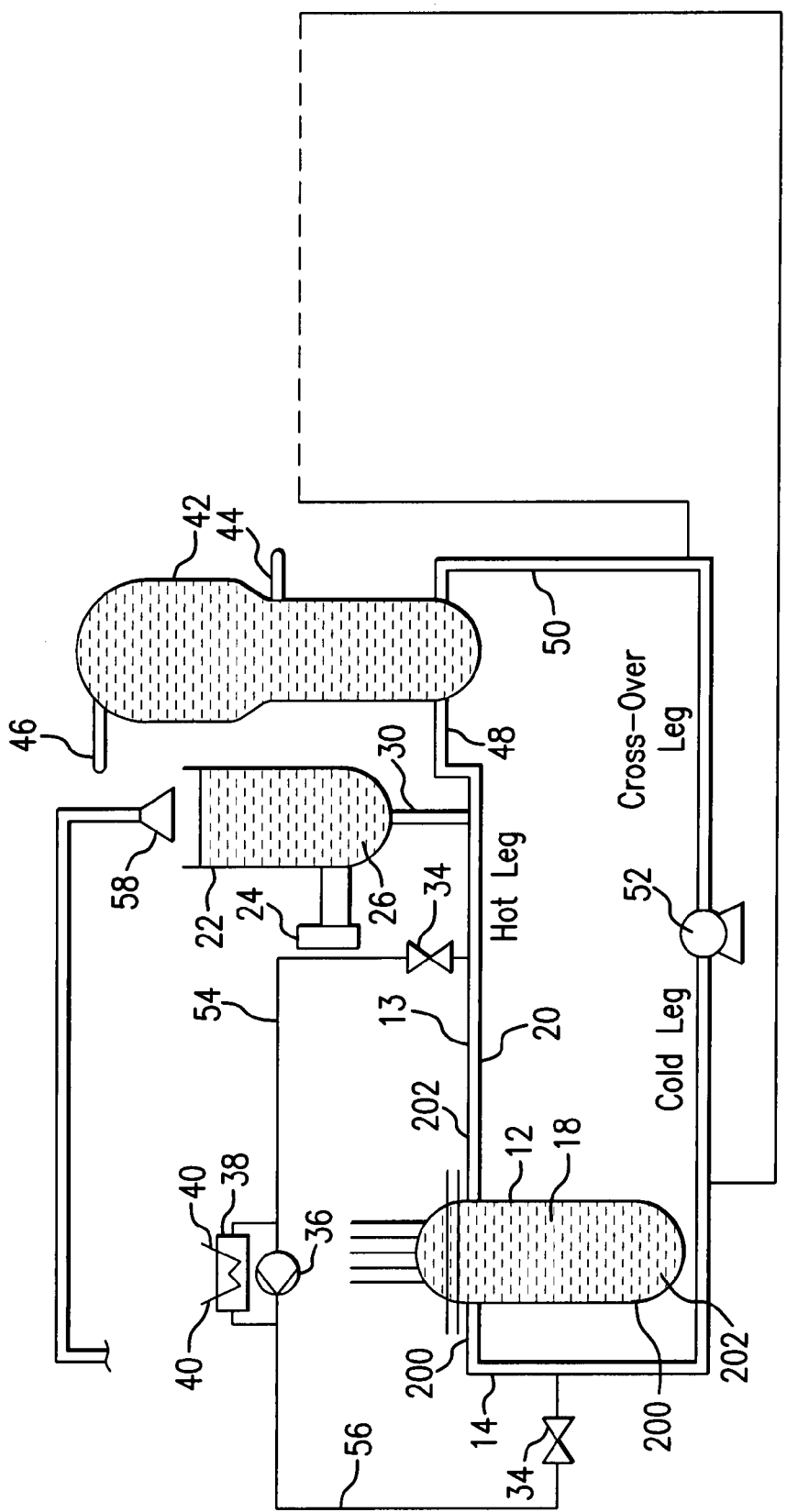
FIG. 1 is an arrangement for positioning electrochemical potential sensors in an exemplary nuclear reactor coolant system of a pressurized water reactor.

Referring to FIG. 1, an electrochemical corrosion potential analyzing system 10 for a pressurized water reactor is illustrated. Although shown in FIG. 1 as relating to pressurized water reactors, the system 10 is equally applicable to boiling water reactors ("BWR"), and thus the example embodiment which is illustrated should not be considered limiting. A nuclear reactor 12 contains nuclear fuel in the form of fuel assemblies 18. The fuel assemblies 18 are located in the reactor 12 such that under prescribed conditions, the nuclear fuel in the fuel assemblies 18 produces a nuclear chain reaction which consequently produces heat. The heat generated by the reaction is removed from the reactor 12 by water flowing in an attached reactor coolant system 13. The water flows in the reactor coolant system 13 from a reactor water inlet 14 into the nuclear reactor 12 and through the nuclear fuel assemblies 18. A reactor outlet 20 allows the warmed water from the reactor 12 to exit the reactor 12 for further processing. The warmed water proceeds out of the reactor outlet 20 and then passes by a pressurizer 22 which maintains pressure and shock control for the reactor coolant system 13. A vapor phase 58 is maintained in a top part of the pressurizer 22 by the actuation of a heater 26 controlled by a heater control unit 24. Water volume in the pressurizer 22 may be modified by adding reactor coolant from a pressurizer surge tank. The pressurizer 22 is connected to the reactor coolant system via a pressurizer surge line 30, which may be straight or bent, (e.g. S bend), through which the pressure and shock control is performed.

The water traveling through reactor outlet 20 passes to the pressurizer through the reactor coolant system steam generator inlet 48. The warmed water passes through the steam generator 42 and transfers the heat to a separate body of water passing from the steam generator secondary inlet 44 to the steam generator secondary outlet 46. The water passing through the steam generator secondary inlet 44 to the steam generator secondary outlet 46 may be transformed to a vapor phase and subsequently passed through a turbine for electrical generating purposes, for example. The water passing through the steam generator 42 exits through a reactor coolant system steam generator outlet 50. The water then returns back through the reactor coolant system 13 to the nuclear reactor 12 by aid of the reactor coolant pump 52. If the control valve 34 allows the warmed water which exits the reactor outlet 20 to the residual heat removal inlet line 54, the warmed water then passes through a residual heat removal pump 36 with a connected heat exchanger 38. The heat of the warmed water may be transferred by a heat exchanger 38 to a separate body of water flowing through an inlet/outlet 40. The water passing through the residual heat removal pump 36 may then be returned to the remainder of the reactor coolant system 13 through a residual heat removal outlet line 56.

Figure 2:
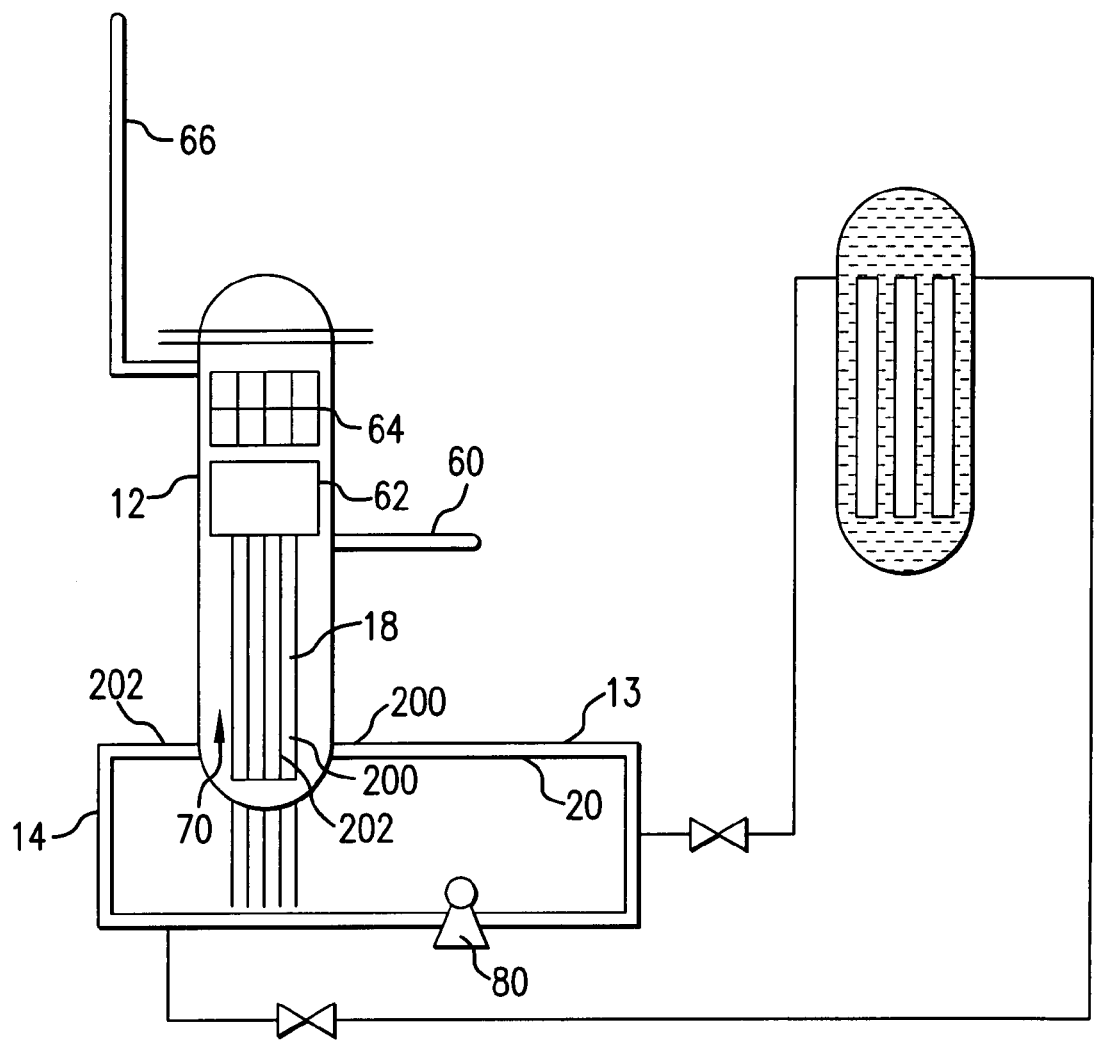
FIG. 2 is an arrangement for positioning electrochemical potential sensors in an exemplary nuclear reactor coolant system of a boiling water reactor.

Referring to FIG. 2, an electrochemical corrosion potential analyzing system for a backward pumped boiling water reactor is illustrated. A nuclear reactor 12 contains nuclear fuel in the form of fuel assemblies 18. The fuel assemblies 18 are located in the reactor 12 such that under prescribed conditions the nuclear fuel in the fuel assemblies 18 produces a nuclear chain reaction by emitting nuclear radiation and heat. The heat, generated by the reaction, is removed from the reactor 12 by boiling water and thus producing steam. The water, which is used for boiling, is transported into the reactor 12 via the feedwater pipe 60. The water may be forced through the fuel assemblies 18 by use of internal jet pumps 70. The water may be transformed into steam when passing through the fuel assemblies 18. The steam then passes through a steam separator 62 and steam dryer 64 to the main steam pipe 66, which leads the steam away from the reactor 12. An average temperature distribution of the water is achieved circulating the water through an external recirculation piping 13. The water is removed from the reactor 12 through a reactor outlet pipe 20. It is then transported through the recirculation pump 80 and is then transported back to the reactor through the reactor inlet pipe 14.

Referring to FIGS. 1 and 2, probes 200,202 of the system 10 may be positioned at multiple locations in the reactor coolant system 13 and reactor 12 and in adjacent systems to measure electrochemical corrosion potential. For example, a system adjacent to the reactor 12 could be an autoclave situated in a bypass circuit (for example, a regenerative heat exchanger), such that reactor coolant could flow through the autoclave in the bypass circuit and the ECP could be measured therein. The probes 200,202 may be positioned in the reactor coolant inlet 14 and the reactor outlet 20 to measure electrochemical corrosion potential in areas close to the reactor 12. The probes 200,202 may also be positioned anywhere in the reactor coolant system 13 for example on zirconium material structures for measuring of the potential. As illustrated, the probes 200,202 may also be installed on the fuel assemblies 18, for example, at a bottom tie plate or nozzle of the assembly.

Figure 3:
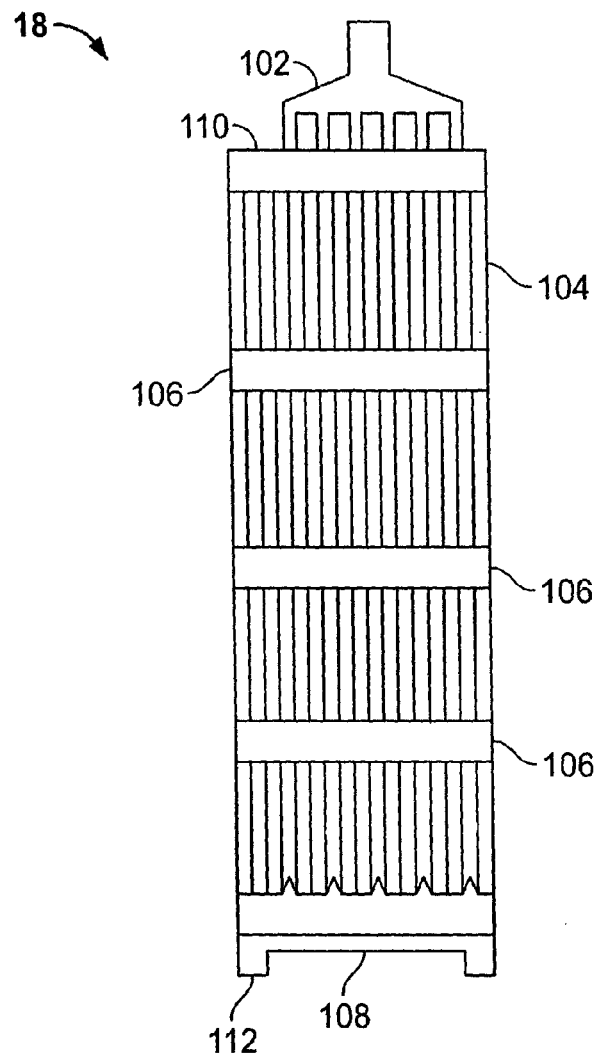
FIG. 3 is a fuel assembly arrangement illustrating zirconium clad fuel rods.

Referring to FIG. 3, an expanded view of a nuclear fuel assembly 18 is illustrated. The nuclear fuel assembly 18 has fuel rods 104 which are comprised of cylindrical fuel elements of enriched uranium dioxide fuel. The enriched uranium dioxide fuel is sheathed in zirconium alloy metal in the form of a rod 104. The typical length of a fuel rod 104 may be, for example, 350 to 450 cm long. The individual fuel rods 104 are maintained in relative position by use of spacers 106 placed at intermediate positions from a fuel assembly top 110 to the fuel assembly bottom 112. Control rods 102 are configured to be inserted in between the fuel rods 104 to slow down the nuclear reaction occurring in the fuel assembly.

During the nuclear reaction process, the zirconium clad may be susceptible to corrosion due to increased levels of dissolved oxygen for example. To accurately measure the susceptibility of the zirconium clad nuclear fuel rods to electrochemical corrosion, the electrochemical corrosion potential system 10 measures the electrochemical corrosion potential of areas inside or outside of the reactor core (and away from the zirconium fuel rods) but nearby enough to the nuclear fuel assemblies to provide a representative value of the electrochemical corrosion potential of the zirconium clad. Preferably, the probes 200,202 (including a heated zirconium electrode) are positioned outside of the reactor 12 where they are close enough to the reactor 12 such that the half-life of the predominant radiolysis products (e.g., hydrogen, oxygen, and/or hydrogen peroxide) is not exceeded when such products reach the probes 200, 202. That is, the probes 200,202 (and the heated zirconium electrode) are preferably located at a position within the reactor coolant system 13 where not less than half of the predominant radiolysis products are still present in the reactor coolant. Such a location of the probes 200,202 (and the heated zirconium electrode) allows for the exact conditions of the zirconium fuel rod to be more closely and accurately reproduced at the measurement position of the probes 200,202, thereby resulting in a more accurate and informative electrochemical corrosion potential measurement by the probes 200,202 (and the heated zirconium electrode). Probes which measure the electrochemical corrosion potential of discrete areas of the reactor coolant system 13 may be placed throughout the reactor coolant system 13 such as at the feedwater inlet 14 and reactor outlet 20 as described in the example embodiment above to allow plant operators to both individually determine the susceptibility of the individual components of the reactor components as well as an entire system overview.

By measuring several components inside or outside of the reactor for the electrochemical corrosion potential, the components closely associated in material type and position would have a similar electrochemical corrosion. For this reason, in the example embodiment described, electrochemical corrosion probes may be placed on the feedwater inlet 14, of the nuclear reactor pressure vessel close to the reactor 12 yet far enough away from neutron flux and heat of the reactor 12. These probes can be configured such that each of the probes measures a voltage which maybe proportional to the electrochemical corrosion potential of the individual metallic components measured. The measured values may then be sent by leads or other arrangements to an arrangement 208, such as a potentiostat and/or computer, configured to receive such voltage inputs. The arrangement 208 may then average the values obtained on the entrance and exit of the reactor or any other location in the reactor or adjacent system to obtain an average value of electrochemical corrosion potential. The arrangement 208 may be located at a remote location from the reactor coolant system 13 to allow operators to monitor electrochemical corrosion potential outside of a radioactive environment.

The electrochemical corrosion system 10 may have a probe with at least two sensors 200, 202 wherein at least one of the sensors has at least one zirconium electrode. In addition, at least one of the sensors may include an electrode comprising a material which corresponds to a structural element of a nuclear power plant besides the zirconium fuel rod. For example, an electrode may comprise stainless steel (such as a 300-series stainless steel), which may correspond to a structural element of the plant such as piping, etc. Thus, by measuring the electrochemical corrosion potential with the electrode comprising a material corresponding to a specific structural element, that structural element would have a similar electrochemical corrosion potential and its suseptiblity to corrosion could therefore be measured.

At least one of the sensors 200,202 has a zirconium electrode such that the zirconium electrode closely matches the material constituents of the fuel rods' zirconium fuel cladding, thereby indicating a corrosion potential of the zirconium cladding material of the fuel elements relative to that of other structural members and piping of the reactor internals. Preferably, the zirconium electrode comprises zircaloy, which is frequently used as the fuel rod cladding material. Preferably, the zirconium electrode is heated to a temperature which is approximately equal to that of the fuel rod surface temperature. Typically, the fuel rod surface temperature will be between approximately 250-400° C., especially between approximately 296-400° C. The heating of the zirconium electrode may be achieved by any conventional means, such as by inserting a heating rod or element into the zirconium electrode. The heating rod or element should have a watt density representative of a nuclear fuel rod such that the zirconium electrode can be heated to a temperature which is approximately equal to that of the fuel rod surface temperature. By heating the zirconium electrode to that of the fuel rod surface temperature, the exact conditions of the zirconium fuel rod are more closely and accurately reproduced at the zirconium electrode, thereby resulting in more accurate and informative electrochemical corrosion potential measurements by the zirconium electrode. Thus, in comparison to any previously known electrodes and methods of use thereof, the heated zirconium electrode of the present invention provides a more accurate measurement of the susceptibility of the zirconium clad nuclear fuel rods to undergo electrochemical corrosion.

The electrochemical corrosion potential measurements may be made by two differing methods. A sensor may provide data for determination of an electrochemical corrosion potential through the application of an external current to a sensor in the probe, wherein after a voltage is then measured between the sensor and a reference sensor. Alternatively, the electrochemical corrosion potential may be determined from data provided by a sensor which is potentiostatically controlled (voltage controlled) (i.e. a voltage differential is created between at least two sensors). A current is then measured between the two sensors. In the instance of a potentiostatically controlled probe with two sensors, the measured current may then be used to calculate a corrosion rate knowing the material type, the area sampled, and the approximate density of the material sampled for example.

Figure 4:
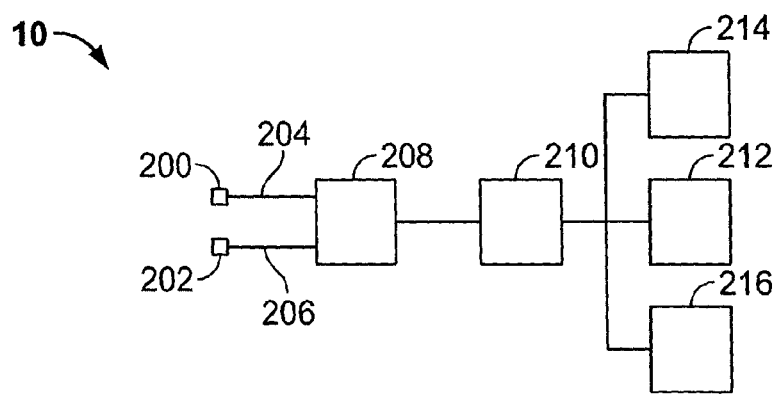
FIG. 4 is an arrangement for measuring an electrochemical corrosion potential in conformance with the present invention.

Referring to FIG. 4, a system 10 for measuring an electrochemical corrosion potential is illustrated. A first probe 200 and a second probe 202 are connected to an arrangement 208. The first probe 200 and the second probe 202 may have internal sensors used for measuring the electrochemical corrosion potential of the surface that the probes 200,202 are installed upon. The arrangement 208 is configured to at least one of establish a voltage differential to the individual first probe 200 and second probe 202 or apply a current to each of the first probe 200 and second probe 202 through respective first 204 and second 206 leads. Each of the first and second leads 204,206 may be placed such that the leads 204,206 are not subject to excessive heat conditions. Additionally, each of the probes 200, 202 connected to the arrangement 208 may be configured with a differing material zirconium alloy, such that a electrochemical corrosion potential for differing material types is determined. The leads 204 and 206 may also be positioned such that potential electrical interference from flowing current and/or voltage is minimized. The leads 204 and 206 extend between the arrangement 208 and the first probe 200 and second probe 202, respectively. The leads 204 and 206 may both send and receive current and/or voltages to and from the probes 200,202 and the arrangement 208. In an alternative configuration, the probes 200,202 may be configured such that transmission of data determined by the probes is performed through wireless technology. The arrangement 208 may be a potentiostat, as a non-limiting example.

The arrangement 208 may also be connected to a computer 210 which may retain data from the probes 200,202. The computer 210 may obtain data from the probes 200,202 on a periodic basis or on a continual basis at the discretion of the operator. The computer 210 may retain the data from the probes 200,202 in a memory or may output the data to an attached printer 212, a data storage device 214 and/or a display device 216. Each of the arrangement 208, computer 210, printer 212, data storage device 214 and/or display device 216 may be located at a remote location from the reactor coolant system 13 in order to allow operators to monitor electrochemical corrosion potential outside of a radioactive environment. In addition, even if such components are not located at a remote location from the reactor coolant system 13, these components may be configured such that transmission of data between these components is performed through wireless technology (i.e., the data can be accessed remotely). The arrangement 208 and the computer 210 may be configured such that more than two probes are connected for data acquisition. The computer 210 may also calculate the amount of corrosive damage to the fuel rods 104 over time, given the calculation of the electrochemical corrosion potential and derived corrosion rate. By performing this calculation of anticipated damage amounts over time, reactor operators are provided with an assessment of acceptable safety margins for the nuclear fuel assembly 18 over time. This consequently allows the reactor operators sufficient time to plan reactor outages as well as predict what work will need to be accomplished during the reactor outage.

The probes 200,202 and associated leads 204,206 may also be installed inside the nuclear reactor such that measurements may be accomplished close to the nuclear reactor fuel assemblies 18. If the probes 200,202 and associated leads 204,206 are installed internally in the reactor pressure vessel 12, the probes 200,202 and leads 204,206 may be designed such that they can withstand the anticipated neutron flux and heat conditions of the reactor 12. The leads 204,206 may be placed through an existing instrumentation penetration in nuclear pressure vessel 12, thereby allowing the system 10 to be installed in existing nuclear power stations without modification. The probes 200,202 may be installed on structural members inside the reactor pressure vessel 12 which contain zirconium alloys, thereby allowing measurements to be obtained. Alternatively, the probes 200,202 may be attached to identifiable sections of fuel assemblies 18, for example the ends of the fuel assemblies such as the external positions of the nozzle 108. The attachment of the probes 200,202 to the reactor 12 is accomplished such that foreign material from the probes 200,202 is excluded from the reactor water coolant stream under normal and accident conditions. In another example embodiment, a probe or individual sensors, for example two sensors, may be positioned internally in the reactor 12, while two sensors remain outside the reactor 12 to provide a reference reading. The measurements obtained by the sensors in the reactor 12 and outside the reactor 12 are then provided to an arrangement such as a potentiostat. The probes 200,202 may extend from a penetration in the bottom of the reactor pressure vessel 12, for example an Instrumentation Thimble penetration, and may be positioned on any lower structure of the reactor 12, for example, the lower core plate, the flow mixer plate or bottom support forging. The computer 210 may then take the data provided to the potentiostat 208 and calculate the electrochemical corrosion potential. The probes 200,202 may be configured such that they can be removed during in-vessel work during a reactor outage such that maintenance of the probes 200,202 does not severely economically impact the operation of the reactor.

As previously described, in a preferred embodiment of the invention, a zirconium electrode is heated to a temperature which is approximately equal to that of the fuel rod surface temperature. In comparison to any previously known electrodes and methods of use thereof, the heated zirconium electrode of the present invention provides a more accurate measurement of the susceptibility of the zirconium clad nuclear fuel rods to undergo electrochemical corrosion. To show the more accurate measurement capabilities of the heated zirconium electrode of the present invention, tests were conducted in the laboratory setting.

To simulate the situation in a typical nuclear power plant at the beginning of a fuel cycle (i.e. without impurities or crud deposits on surfaces), a laboratory recirculation loop was used, equipped with all of the necessary means to control water chemistry at inlet and outlet (e.g., conductivity, $O_2$ level, $H_2$ level, etc.). In addition, a controlled dosage pump was provided in the recirculation loop to provide for a specified impurity level, if needed.

Figure 6:
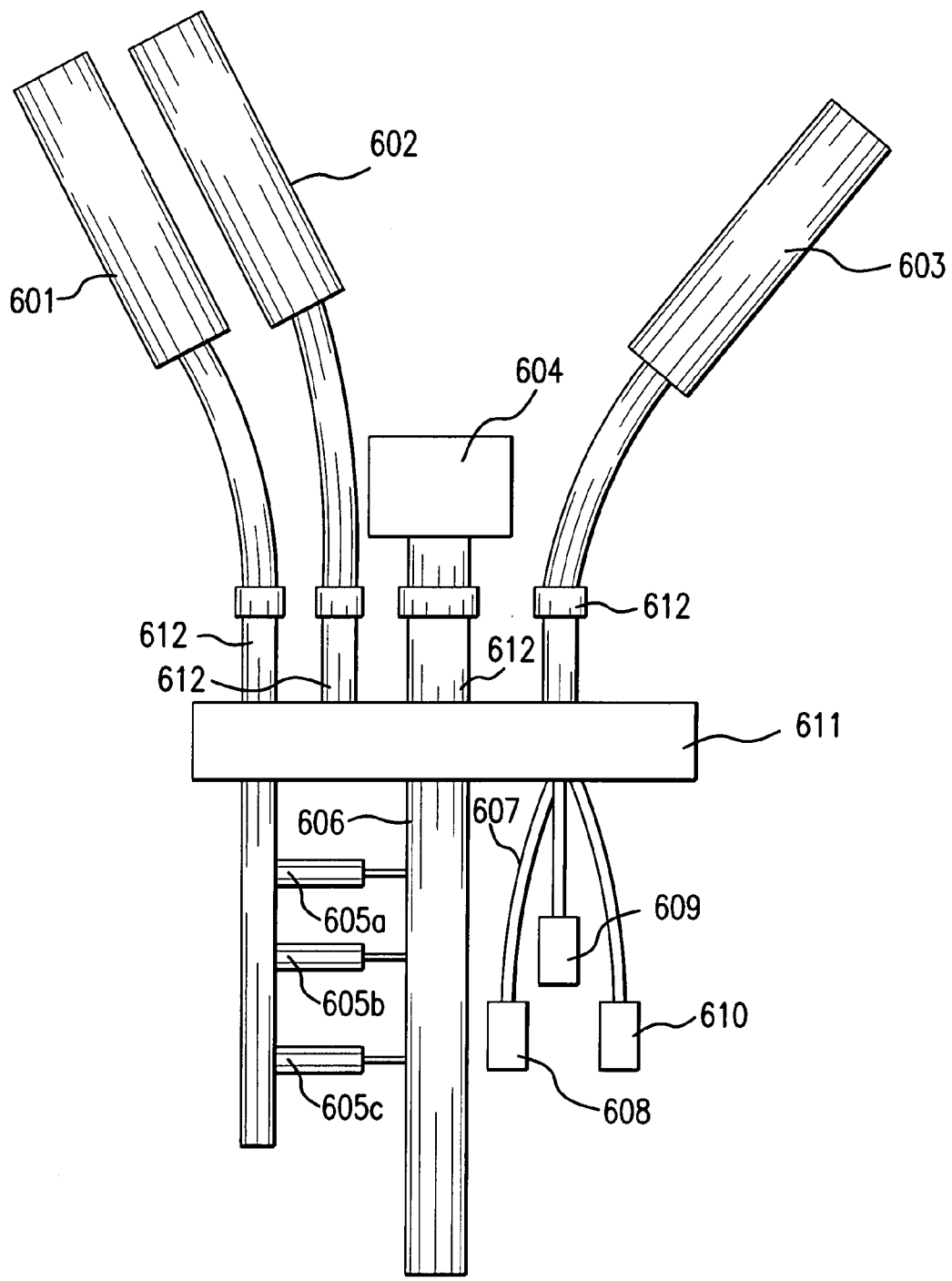
FIG. 6 is a schematic illustration of the electrodes and components used in an autoclave as tested in a laboratory setting (walls of autoclave not shown).

A heating rod inserted into the zircaloy fuel cladding was employed to create heated zirconium surfaces at 70 $W/cm^2$, which is the typical heating level existing in BWR. Several electrodes were used to measure the ECP of the zircaloy fuel rods: a heated zircaloy electrode (heated to the fuel rod surface temperature), an unheated type 347 stainless steel electrode and an unheated zircaloy electrode. A platinum electrode was used to measure the redox potential of the electrolyte, and a high temperature Ag/AgCl electrode was used as a reference electrode. The assembly was installed in a recirculation 1-liter autoclave in order to simulate (at smaller scale) the recirculation autoclave which would be adjacent to the nuclear reactor (e.g., situated in immediate proximity of the outside of the reactor vessel), as shown in FIG. 6.

The recirculation 1-liter autoclave was equipped with specially fitted cooling jackets 601, 602, 603 and 604 on the lid 611 of the autoclave for cooling the electrical penetration to the heated zircaloy electrode 606 (inside the zircaloy tube) and the high temperature Ag/AgCl reference electrode 607. The electrodes went through the autoclave lid 611 via openings 612.

The temperature of the heated zircaloy electrode was measured in three different areas by three thermocouples 605a, 605b and 605c brought close to the surface of the heated zircaloy electrode by a dip tube attached to the autoclave lid 611. The dip tube had small steel ligaments welded to it to keep the thermocouples in immediate contact with the heated zircaloy electrode during the testing. Their position was such that the temperature measurement was performed in the middle of the heated area (by the middle thermocouple) where the ECP measurement was performed, and in the unheated areas (upper thermocouple and lower thermocouple). The distance between the middle thermocouple and the thermocouples in the unheated areas was equal and approximately 4 cm. The width of the heated area inside of the heated zircaloy electrode was 8 cm and was equally distributed around the position of the central thermocouple. As can be seen by this example of a heated zirconium electrode, only the ECP measurement portion of the zirconium electrode needs to be heated in accordance with the present invention (i.e., only that portion of the zirconium electrode which will be measuring the ECP needs to be heated, preferably to a temperature which is approximately equal to that of the fuel rod surface temperature (the rest of the zirconium electrode may also be heated, but it is not required)).

Inside the recirculation 1-liter autoclave, the platinum electrode 609 for measurement of the redox potential was approximately equally distanced at a 2 cm distance from the heated zircaloy electrode 606, from the unheated 347 SS electrode 610 and from the unheated zircaloy electrode 608. The size of the surface areas of each of the electrodes is presented in Table 1.

TABLE 1

Surface Area of Electrodes used in the recirculation 1-liter autoclave

| Electrode | Surface Area ($cm^2$) |
|---|---|
| heated zircaloy electrode | 48 $cm^2$ |
| unheated zircaloy electrode | 7 $cm^2$ |
| unheated SS 347 electrode | 5.2 $cm^2$ |
| high temperature reference electrode (Ag/AgCl) | N/A |
| platinum electrode | 3.1 $cm^2$ |

The relative distances of the electrodes to the high temperature Ag/AgCl reference electrode is presented in Table 2.

TABLE 2

Relative Distance of the Electrodes to the High Temperature Ag/AgCl Reference Electrode

| Electrode | Distance to the High Temperature Ag/AgCl Reference Electrode (cm) |
|---|---|
| heated zircaloy electrode | ~1 cm |
| unheated zircaloy electrode | ~2 cm |
| unheated SS 347 electrode | ~1 cm |
| platinum electrode | N/A |

The corrosion potential measurements were performed under BWR pressure and temperature conditions (i.e., 288° C. fluid exit temperature, 86 bar, with a surface temperature of the heated zircaloy electrode of 296° C.). Furthermore, a number of different chemistry conditions were run during the testing:

inert water conditions;

hydrogen injection in three steps from 0.68 ppm to 1.6 ppm;

oxygen injection in three steps from 2.2 ppm to 8 ppm; and methanol 2 ppm and oxygen 2 ppm in a close loop (without methanol refreshing).

Figure 5:
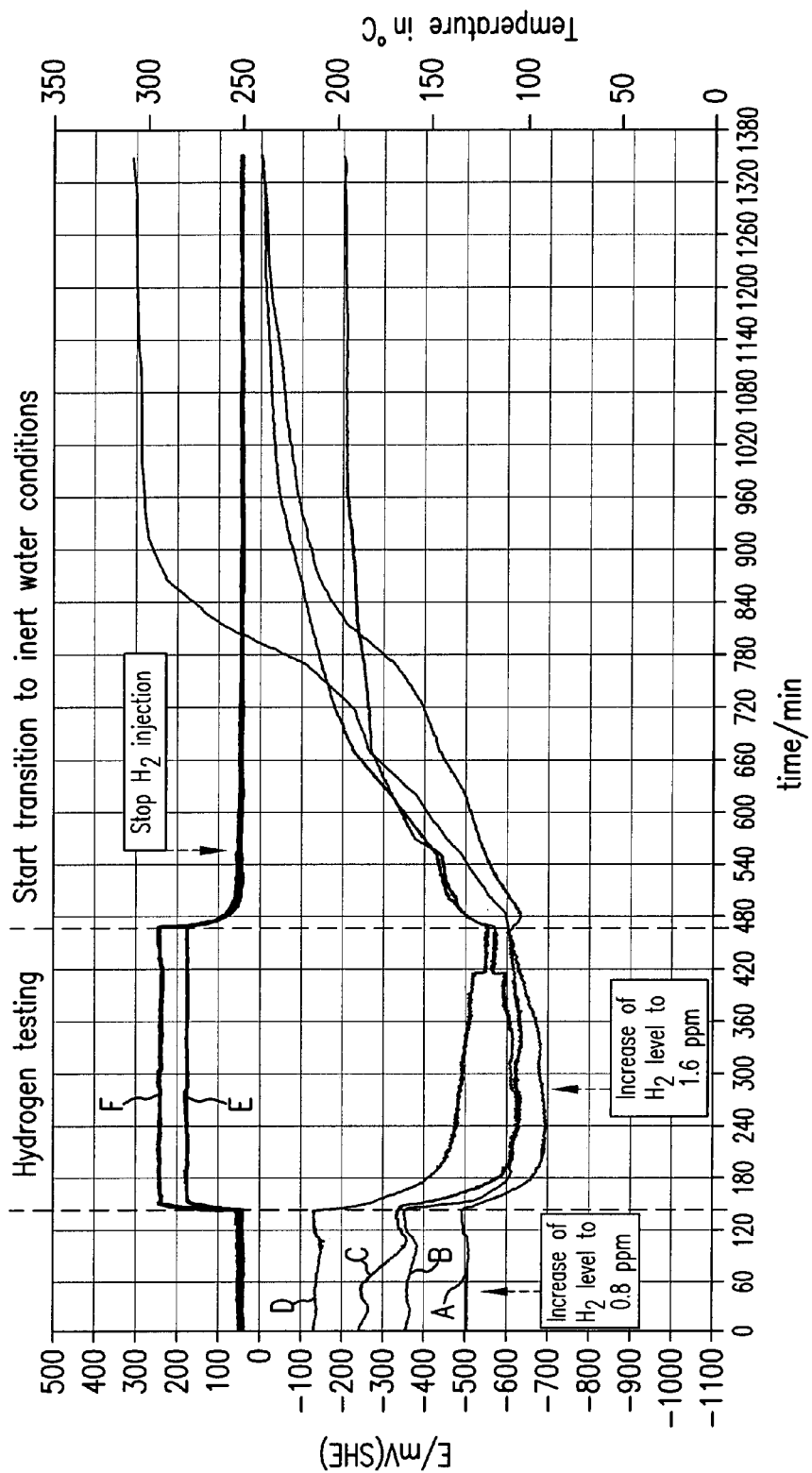
FIG. 5 is a graph illustrating the electrochemical corrosion potential of several electrodes, including a heated zirconium electrode, as tested in a laboratory setting.

The measurements of the ECP by the different electrodes during the course of hydrogen injection are presented in FIG. 5. Curve A represents the ECP measured by a Pt electrode (vs. a standard hydrogen electrode (SHE)) which is at the temperature of the medium (i.e., the coolant water in the autoclave), curve B represents the ECP measured by the unheated zircaloy electrode (vs. SHE), curve C represents the ECP measured by the unheated SS347 electrode (vs. SHE), and curve D represents the ECP measured by the heated zircaloy electrode (vs. SHE) (heated to the fuel rod surface temperature). Curves E and F show the temperature of the medium and of the heated zircaloy electrode, respectively. The testing was run under three different water conditions: $H_2$ level=0.8 ppm; $H_2$ level=1.6 ppm; and inert water conditions.

As can be seen from FIG. 5, when the temperature of the zircaloy electrode is increased (i.e., the zircaloy electrode is heated) to the temperature of the fuel rod surface (296° C.), and the $H_2$ level in the coolant water is increased to 1.6 ppm (making corrosion more likely), the resulting ECP measured by the heated zircaloy electrode (curve D) is much higher than the ECP measured by the unheated electrode of the same material (curve B). In fact, curve D is approximately 100 E/mV higher than curve B in this area of the graph, which is a considerable difference in terms of corrosion rate. Thus, these results show that a heated zirconium electrode provides a much more accurate value of the ECP (for a zirconium fuel rod) than does an unheated zirconium electrode, thereby providing a much more informative indicator of whether corrosion is likely to occur.

As can also be seen from FIG. 5, curve B (representing the ECP measured by the unheated zircaloy electrode) and curve C (representing the ECP measured by the unheated SS347 electrode) largely coincide with one another during the portion of the testing wherein the $H_2$ level in the coolant water was increased to 1.6 ppm. This indicates that using either zirconium or stainless steel electrodes in an unheated condition produces very similar ECP results, such that neither seems to be more indicative of susceptibility to excessive corrosion or to stress corrosion cracking.

The present invention provides an electrochemical corrosion potential system that allows for determination of an electrochemical corrosion potential for nuclear fuel rods during an entire fuel cycle of a nuclear power plant. The proximity of the placement of the probes to the fuel assemblies and the heating of the zirconium electrode allow for the calculation of electrochemical corrosion potential for the zirconium cladding of the fuel assemblies unachievable by other systems. Replacement and maintenance costs of the present invention allow the operators of the facility to accurately monitor the corrosion potential, while providing minimal economic impact on the facility.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than in a restrictive sense.

What is claimed is:

1. A method for determining an electrochemical corrosion potential representative of the electrochemical corrosion potential of zirconium cladding of zirconium fuel rods in a nuclear reactor, the method comprising:

positioning at least two electrochemical corrosion sensors in either a nuclear reactor or in a system adjacent to the nuclear reactor, the at least two electrochemical corrosion sensors positioned in and in contact with the reactor coolant in the nuclear reactor or in and in contact with the reactor coolant in the system adjacent to the nuclear reactor, wherein at least one of the at least two electrochemical corrosion sensors includes a heating element and a zirconium electrode in contact with the coolant, said heating element configured to heat said zirconium electrode to a temperature that is approximately equal to a temperature of a surface of zirconium cladding of the fuel rods;

producing a voltage between the at least two electrochemical corrosion sensors;

measuring a current induced by the voltage; and determining an electrochemical corrosion potential representative of the electrochemical corrosion potential of zirconium cladding of zirconium fuel rods based upon the current induced.

2. The method of claim 1, wherein the zirconium electrode is heated to a temperature in the range of approximately 250° to 400° C.

3. The method of claim 1, wherein the zirconium electrode is heated to a temperature in the range of approximately 296° to 400° C.

4. The method of claim 1, wherein the at least two electrochemical corrosion sensors are positioned in the nuclear reactor.

5. The method of claim 4, wherein the positioning of the at least two electrochemical corrosion sensors are one of on a bottom and on a top of a nuclear fuel assembly.

6. The method of claim 1, wherein the at least two electrochemical corrosion sensors are positioned in a system adjacent to the nuclear reactor.

7. The method of claim 4, wherein the zirconium electrode is heated to a temperature in the range of approximately 250-400° C.

8. The method of claim 6, wherein the zirconium electrode is heated to a temperature in the range of approximately 250-400° C.

9. The method of claim 6, wherein the at least two electrochemical corrosion sensors are close enough to the nuclear reactor such that the half-life of a predominant radiolysis product is not exceeded when the product reaches the at least two electrochemical corrosion sensors.

* * * * *